(12) United States Patent
Wan et al.

(10) Patent No.: US 7,998,705 B2
(45) Date of Patent: Aug. 16, 2011

(54) INCREASED DYNAMIC BINDING CAPACITY IN ION EXCHANGE CHROMATOGRAPHY BY ADDITION OF POLYETHYLENE GLYCOL

(75) Inventors: Min Wan, Cary, NC (US); Mark David Chavez, Raleigh, NC (US); Jeffrey Lee Schrimsher, Hillsborough, NC (US)

(73) Assignee: FUJIFILM Diosynth Biotechnologies U.S.A., Inc, Morrisville, NC (US)

( * ) Notice: Subject to any disclaimer, the term of this patent is extended or adjusted under 35 U.S.C. 154(b) by 2030 days.

(21) Appl. No.: 10/292,950

(22) Filed: Nov. 12, 2002

(65) Prior Publication Data

US 2004/0030107 A1    Feb. 12, 2004

Related U.S. Application Data

(60) Provisional application No. 60/401,570, filed on Aug. 6, 2002.

(51) Int. Cl.
*C12P 21/04*    (2006.01)
*C07K 1/18*    (2006.01)

(52) U.S. Cl. ...... 435/71.1; 435/70.1; 530/344; 530/416; 530/417

(58) Field of Classification Search ............... 435/70.1, 435/71.1; 530/344
See application file for complete search history.

(56) References Cited

U.S. PATENT DOCUMENTS

| | | | | |
|---|---|---|---|---|
| 4,624,918 A | * | 11/1986 | Hershberg | 435/70.1 |
| 5,151,358 A | | 9/1992 | Heinsohn et al. | 435/226 |
| 5,695,958 A | * | 12/1997 | Builder et al. | 435/69.1 |
| 5,723,310 A | * | 3/1998 | Builder et al. | 435/69.1 |
| 5,798,227 A | * | 8/1998 | Hoffman et al. | 435/69.6 |
| 6,005,081 A | * | 12/1999 | Burton et al. | 530/399 |
| 6,162,782 A | * | 12/2000 | Clarkson et al. | 510/320 |
| 6,184,360 B1 | * | 2/2001 | Burton et al. | 530/399 |
| 6,383,393 B1 | | 5/2002 | Colpan et al. | |
| 6,403,362 B1 | * | 6/2002 | Moriya et al. | 435/254.1 |
| 6,869,932 B2 | * | 3/2005 | Veronese et al. | 514/12 |
| 7,531,645 B2 | * | 5/2009 | Basey et al. | 530/416 |

FOREIGN PATENT DOCUMENTS

WO    WO 95/01359    1/1995

OTHER PUBLICATIONS

Karger, S. Vox Sang vol. 49, 1985 pp. 240-243.*
P. Gagnon et al. "Method for obtaining unique selectives in ion-exchange chromatography by addition of organic polymers to the mobile phase" Journal of Chromatography, vol. 743; pp. 51-55 (1996).
K. Milby et al. "Ion-Exchange Chromatography of Proteins The Effect of Neutral Polymers in The Mobile Phase" Journal of Chromatography, vol. 482; pp. 133-144 (1989).
Y. Papanikolau et al. "Solubility, crystallization and chromatographic properties of macromolecules strongly depend on substances that reduce the ionic strength of the solution" Protein Engineering, vol. 10; No. 8 pp. 847-850 (1997).
Feng et al. "Polyethylene glycol improves the purification of recombinant human tumor necrosis factor during ion exchange chromatography," Biotechnology Techniques vol. 12(4) pp. 289-293 (1998).
PCT International Search Report dated Feb. 4, 2004 for corresponding PCT Application No. PCT/US03/24485.

* cited by examiner

*Primary Examiner* — Herbert J. Lilling
(74) *Attorney, Agent, or Firm* — Morgan, Lewis & Bockius LLP

(57)    ABSTRACT

The present invention generally relates to novel processes for protein purification in high salt solutions such as cell culture broth by increasing the dynamic binding capacity of a resin with the addition of polyethylene glycol.

23 Claims, 6 Drawing Sheets

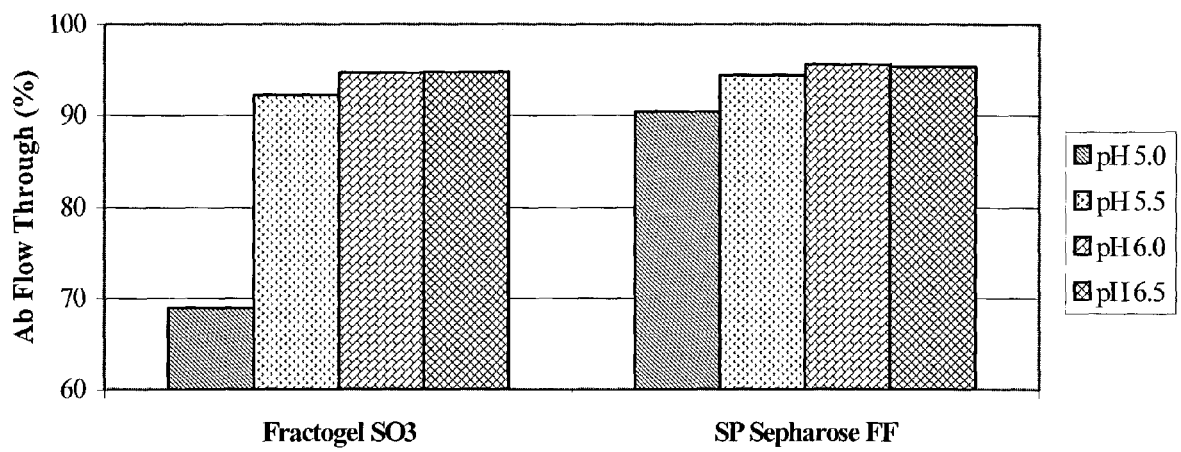
Fig. 1. pH Effect on Loading Capacity
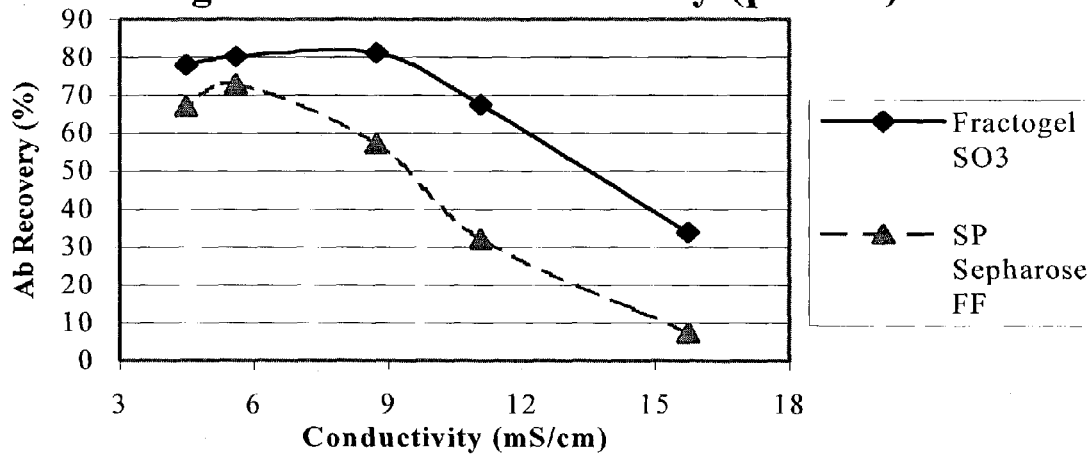
Fig. 2. Load Dilution Study (pH 5.0)

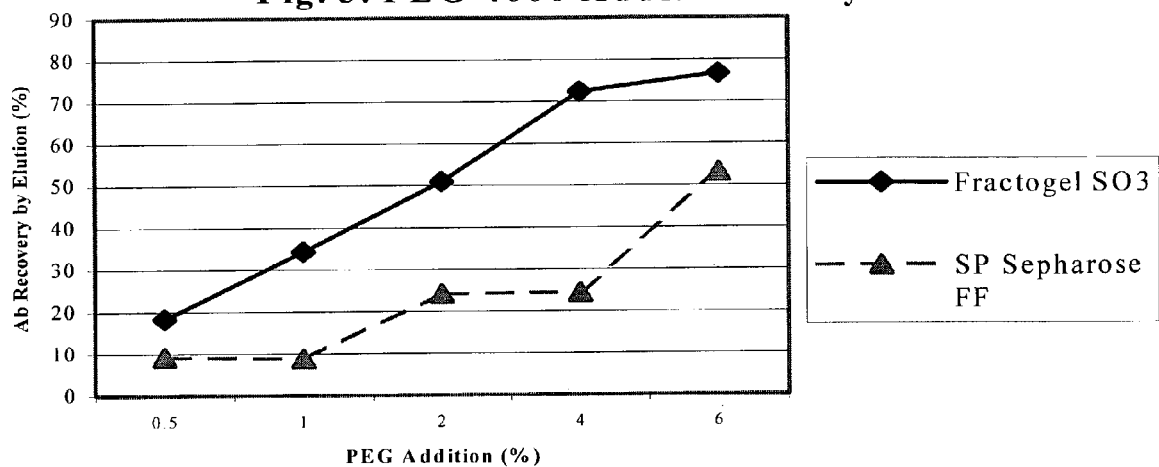
Fig. 3. PEG 4600 Addition Study
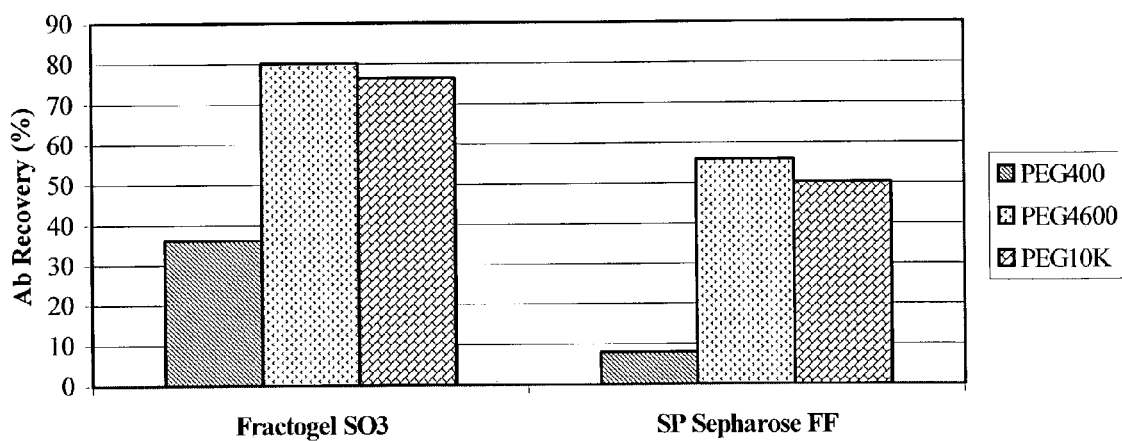
Fig. 4. PEG Type Study

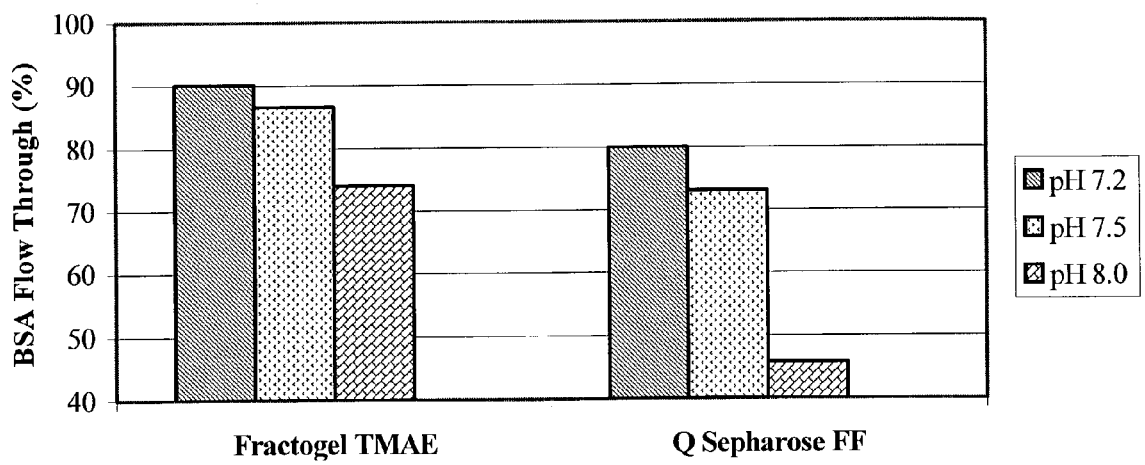
Fig. 5. pH Effect on BSA Loading Capacity
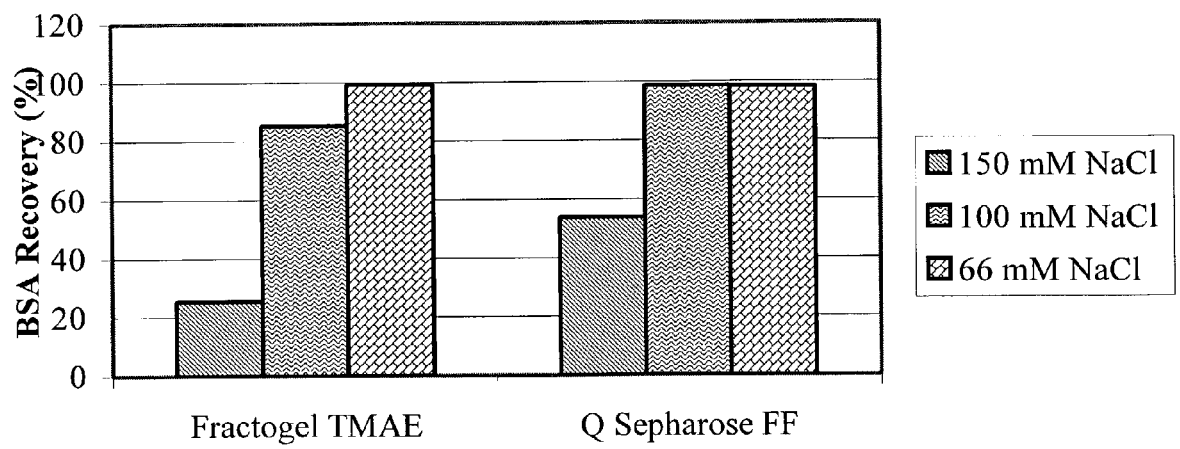
Fig. 6. BSA Loading Dilution Study

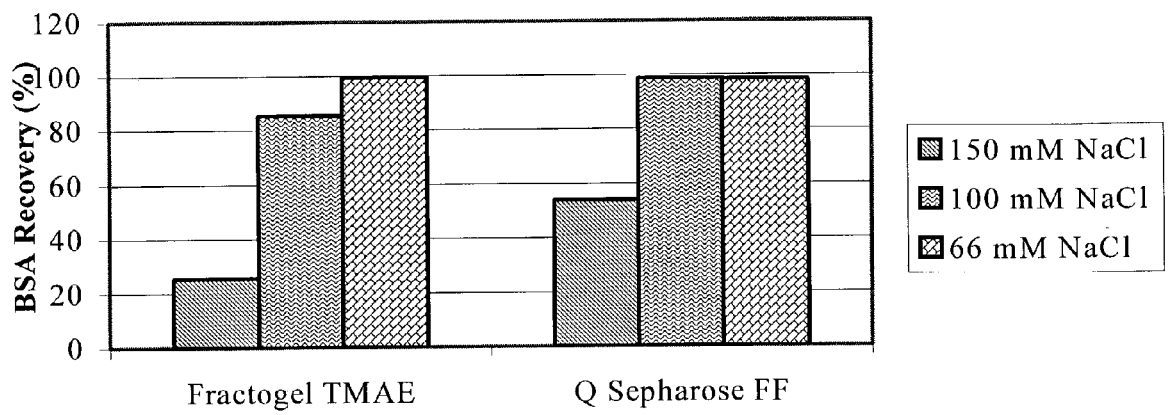
Fig. 7. BSA Loading Dilution Study
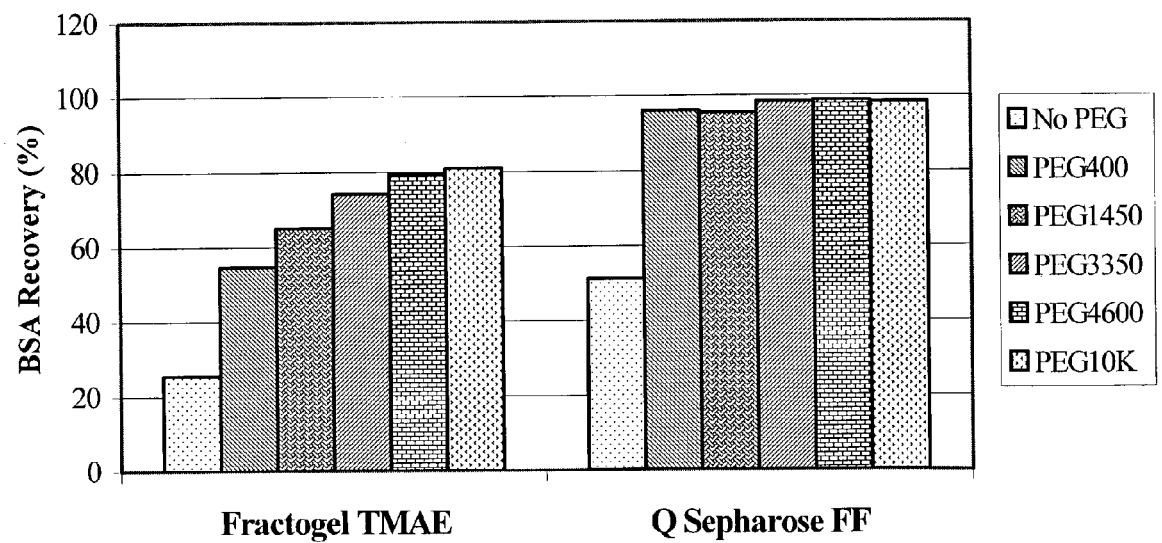
Fig. 8. BSA PEG Type Study

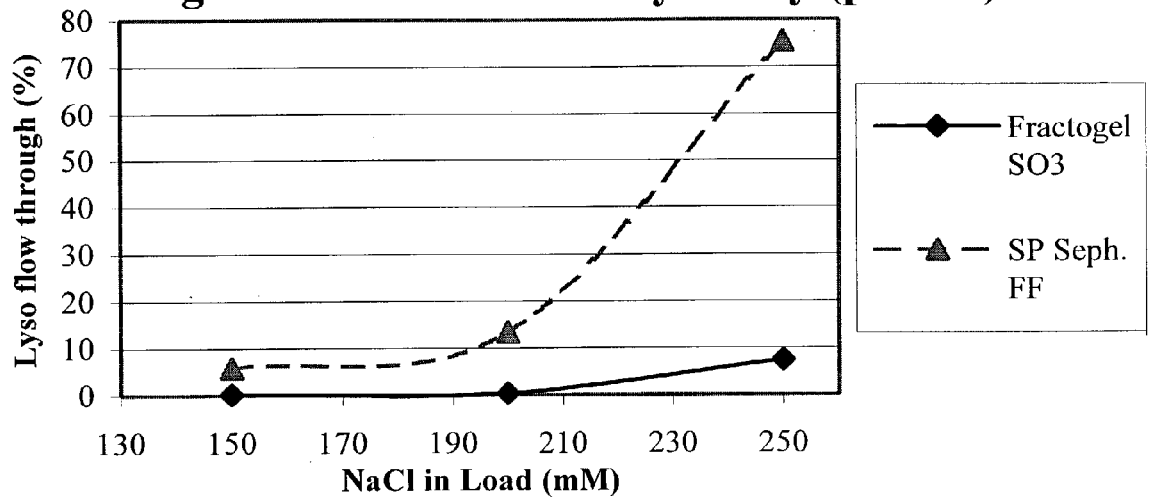
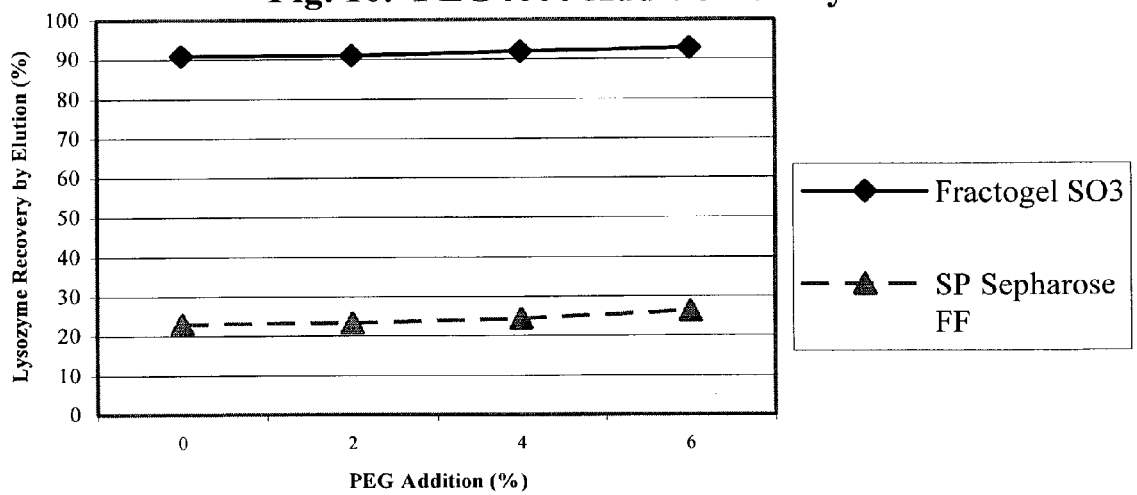

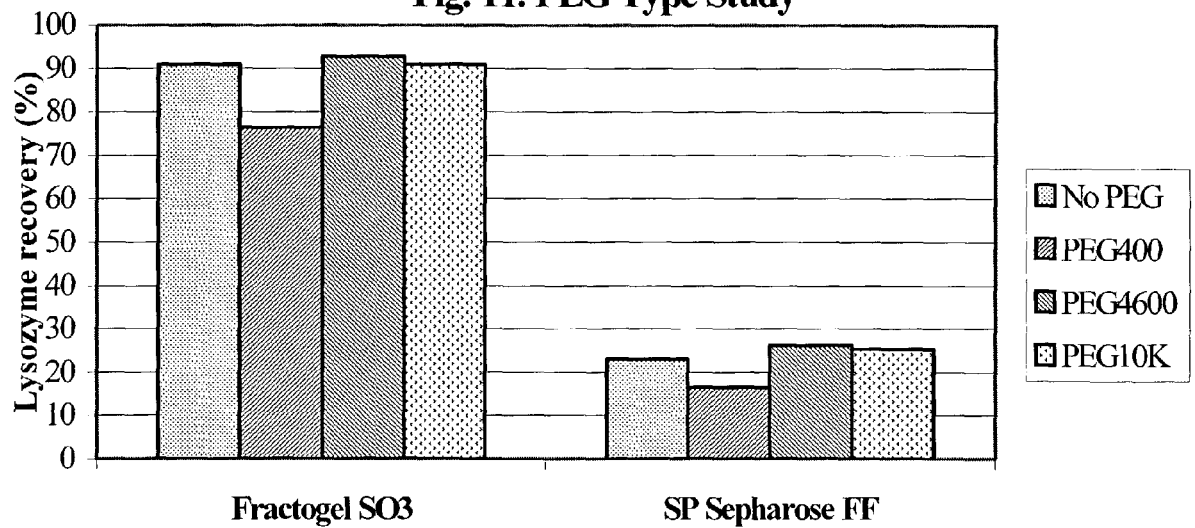
Fig. 11. PEG Type Study

US 7,998,705 B2

INCREASED DYNAMIC BINDING CAPACITY IN ION EXCHANGE CHROMATOGRAPHY BY ADDITION OF POLYETHYLENE GLYCOL

RELATED APPLICATION

This application is related to provisional application Ser. No. 60/401,570, filed on Aug. 6, 2002, titled Increased Dynamic Binding Capacity in Ion Exchange Chromatography by Addition of Polyethylene Glycol.

FIELD OF THE INVENTION

Embodiments of the present invention generally relate to processes and compositions comprising an increased dynamic binding capacity in an ion exchange chromatography column to facilitate the loading of proteins.

BACKGROUND OF THE INVENTION

Ion exchange chromatography is one of the most widely used methods for separating, identifying and/or quantifying amounts of proteins and/or peptides in a mixture or solution. The technique primarily exploits differences in the sign and magnitude of the net electric charges of peptides and/or proteins at a given pH. These values are predictable from the associated $pK_a$ value and/or titration curve. See *Principles of Biochemistry*, Lehninger et al. (New York, 1997, p. 122).

Commonly, a chromatographic column consists of a tube at least partially filled with particles of a synthetic resin containing fixed charged groups. Those with fixed anion groups are called cation-exchange resins. Those with fixed cation groups are called anion-exchange resins. Separation of peptides and/or proteins can occur by gradually changing the pH and/or salt concentration of a solution being run through a column.

An ion exchangers operation is dependent upon certain properties of the system. Each property has an effect on the efficiency and productivity of an ion exchanger. Properties of an ion exchange column that affect operation include, but are not limited to:

Density: The density of resin has an affect upon how the system performs. Properties of resin should be understood. For example, the density of a dry, water free resin is generally smaller for anion exchangers than cation exchangers. The density of water swollen resin depends on the type counter ion, swelling capacity and on the degree of crosslinking, besides the density of dry resin. Furthermore, it should be noted that bulk density is different than the density of the swollen resin. These densities are important because operation is typically dependent upon the resins.

Mechanical resistance: the mechanical resistance is a variable that is studied for ion exchangers. The mechanical resistance is found to vary with structure of the system. It should be noted that air dried resin is destroyed by certain friction. This needs to be thought of in design stages.

The particle size, is a major part of the fluid flow and effectiveness of separation processes. For example, condensation type resins are generally broken granules. On the contrary, polymerization-type resins are small beads that are uniformly packed. To measure the particle size a mesh is used to differentiate larger particles. For separations such as chromatography, particle size can be extremely important to efficiency, especially in regards to resolution of different species. Particle size also largely determines the fluid resistance of an ion exchange column. This can be the key to success of an industrial operation.

The total capacity is a measurement tool used to rate an ion exchanger. The total capacity is the amount of exchangeable ions of unit weight of resin, commonly expressed as ligand density. The determination of such factor can be done by acid-base titration. Another capacity measurement is salt splitting. This is the amount of sodium ions absorbed by the cation exchanger in the hydrogen form from a sodium chloride solution or hydrogen released by unit weight or unit volume. For an anion exchanger the amount of base liberated from a salt by unit weight or unit volume of the hydroxyl-form anion-exchange resin. Dissociation constants of active groups of the resin are a major part of the salt splitting capacity. Further, noted is the rest capacity which consists of the difference in mono-functional strongly acidic or basic resin of splitting capacity. Also, the apparent capacity can be defined as the effects of multivalent ions on an ion exchanger. Further, the break-through capacity depends on the pH, particle size, column size and flow-rate. Knowing and understanding the capacities allows for proper design of the system properties.

The porosity of a system controls much of the capacity of the exchanger. The surface active groups and capillary groups take part in the characteristics of a ion exchanger. The pores of ion exchangers are typically of variable size even for the same resin product. The determination of porosity can be done by means of solution containing ions of known size and similarity by using capacity measurements. Also, the same measurement can be done by the use of vapor pressures. Although these methods only measure mean particle size, it results in useful knowledge. In addition to the above, it should be noted that the degree of crosslinking affects mean pore size.

Throughput: Throughput is an important aspect when considering operational costs and efficiency. Knowing the effects of controlling the flow is desirable also. For example, it is accepted in the art that natural zeolite exchangers operate slower and an ion exchanger of larger pores quicker. As well, a cation exchanger is also known in the art to equilibrate more quickly. The diffusivity is a controlling factor in determining the operating rate. In addition, the rate depends on diffusivity constants of active groups of the resins. However, other influencing factors include, but are not limited to, temperature, solution viscosity, resin density, particle size and distribution, and degree of crosslinking in the resin.

There have been numerous ion exchange chromatography systems established. Each has certain benefits and each has resulted in certain limitations. Ion exchange chromatographic columns are a commonly used step for protein purification. However, the use of ion exchange chromatography is often limited by solutions containing excessive amounts of competing ions for the binding sites. For example, the salt concentration in the loading feed stream from harvested cell culture broth frequently prevents the protein of interest from binding to the resin. This application of an ion exchange column demonstrates the purification of a target molecule in the presence of high salt, in particular product from harvested cell culture broth.

Examples from the prior art include an article by P. Gagnon et al. in the Journal of Chromatography in 1996, vol. 743 (1), pp. 51-55, that disclosed the addition of polyethylene glycol (PEG) to the mobile phase of a column (the phase traveling through the column). The article disclosed that the addition of the PEG altered the retention behavior of proteins and produced unique selectivity in ion-exchange chromatography. However, the article further disclosed that the secondary effects of increased viscosity from addition of PEG severely limited the preparative potential for application of this technique, i.e. elevated viscosity reduced flow-rate. Moreover, the increased viscosity was disclosed as severely depressing the dynamic binding capacity for small proteins, even though the dynamic binding capacity appeared to be maintained or slightly increased for large ones. Likewise, the article disclosed that the PEG addition substantially increased peak width.

Accordingly, the Gagnon article does not disclose a chromatographic system wherein an addition of PEG increases dynamic binding capacity for proteins. Particularly, this article does not disclose a system wherein an addition of PEG increases the dynamic binding capacity for systems with small proteins while reducing process time.

An article authored by K. Milby et al., in the Journal of Chromatography (1989, vol. 482 (1), pp. 133-44), further discloses the addition of PEG to an eluent that increased retention time on tested proteins. However, significant operation pressure increase was observed because of the viscosity of the mobile phase. Importantly, the Milby article does not disclose the addition of PEG in a load feed stream of an ion exchange column.

An article authored by Y. Papanikolau et al., in Protein Engineering (1997, vol. 10 (8), pp. 847-850), makes theoretical assumptions of PEG addition in protein solutions. However, the article failed to state any experimental results or present any other data that would lead one of ordinary skill in the art to add PEG to a load stream in an ion exchange column.

An article authored by Feng et al., in Biotechnology Techniques (1998, vol. 12 (4), pp. 289-293), discloses the purification of human tumor necrosis factor-α using anion exchange chromatography. The authors observed that the column binding capacity increased by adding PEG to the buffer and feed solution. The optimum concentration was 1% with PEG 200. However, the Feng article did not disclose the addition of PEG to a protein solution for loading in high salt concentrations.

An article authored by H. Bioerlinq in Vox Sang (1985, vol. (49), pp. 240-243), discloses the isolation of human albumin using a PEG step precipitation. The author observed that all the proteins in the plasma preparation were bound to the DEAE Sepharose gel in the presence of the high salt concentration and with a much higher binding capacity than without PEG. However, the Bioerling article utilizes a PEG concentration of 10% w/w. This severely restricts the application in terms of both solution viscosity and also losses due to precipitation.

U.S. Pat. No. 5,151,358 discloses the recovery and purification of chymosin using a PEG liquid-liquid two-phase separation. The PEG rich product containing profile was than loaded to an ion exchange column. There was no data reported. Moreover, the two-phase extraction appeared to be in low salt concentrations.

Accordingly the art field is in search of a process whereby an ion exchange column may be utilized for the purification of product in the presence of high salt, in particular from harvested cell culture broth, thereby allowing a product of interest to bind to a resin.

SUMMARY OF THE INVENTION

Embodiments of the present invention generally relate to processes and compositions comprising an increased dynamic binding capacity in an ion exchange chromatography column to facilitate the loading of proteins by the addition of polyethylene glycol to the load stream.

BRIEF DESCRIPTION OF THE FIGURES

FIG. 1 is an illustration of pH effect on loading capacity of bovine γ-globulin on a Fractogel SO3 resin and a SP Sepharose FF resin.

FIG. 2 is an illustration of recovery of bovine γ-globulin on both tested resins from FIG. 1.

FIG. 3 is an illustration of recovery of bovine γ-globulin on both tested resins from FIG. 1 with PEG addition.

FIG. 4 is an illustration of recovery of bovine γ-globulin on both tested resins from FIG. 1 with PEG addition at varying concentrations.

FIG. 5 is an illustration of pH effect on loading capacity of BSA on a Fractogel TMAE resin and a Q Sepharose FF resin.

FIG. 6 is an illustration the recovery of BSA with different sodium chloride concentrations.

FIG. 7 is an illustration of a BSA loading dilution study with varying salt concentration.

FIG. 8 is an illustration of a BSA loading dilution study with varying PEG particle size.

FIG. 9 is an illustration of a load conductivity with lysozyme at pH 7.0 on a Fractogel SO3 resin and SP Sepharose FF resin.

FIG. 10 is an illustration of PEG binding capacity with lysozyme on a Fractogel SO3 resin and SP Sepharose FF resin.

FIG. 11 is an illustration of lysozyme loading dilution study with varying PEG particle size.

DETAILED DESCRIPTION OF THE INVENTION

As used herein, the term "ionic resin" means and refers to any support or supportable medium which is charged, either having gained one or more electrons to form a negatively charged ion, and/or specie, or having lost one or more electrons to form a positively charged ion, and/or specie.

As used herein, "an acceptable amount of precipitation" is such that the precipitation would not adversely interfere with binding of the protein to the resin or have a significant impact on yield.

In its most general terms, the present invention relates to novel processes and compositions for protein purification. Preferred embodiments of the present invention are capable of functioning in high salt solutions. Examples of high salt solutions are those solutions in a cell culture broth. A cell culture broth of the present invention may be a cell culture for any cells. In an embodiment, the cell culture is a cell culture for CHO cells. In another embodiment, the cell culture is a culture for NSO cells. In another embodiment, the cell culture is a rat liver cell. Typically, target molecules in cell cultures have been difficult to separate with ion exchange chromatography because the high salt concentration and/or high conductivity interferes with the protein's binding to the resin.

Embodiments of the present invention generally increase the dynamic binding capacity of an ion exchange resin in a high salt solution by adding polyethylene glycol (PEG) to the high salt solution; and, loading the resin (i.e. contacting the resin with at least one protein to be purified, typically in solution) with the high salt solution. In an embodiment, a protein is added to the solution. In an embodiment, the solution is a cell culture broth and the protein is therein.

Any PEG source may be used and there are no molecular weight exclusions. Generally, a molecular weight PEG is chosen that is as low as possible while suitably increasing the dynamic binding capacity of the resin because PEG, when too large and/or in too great of a concentration, adds to the viscosity of the solution. However, with varying embodiments, any molecular weight PEG may be used.

It has generally been found that the greater the molecular weight of the PEG, the greater the dynamic binding potential. However, this relationship varies slightly for every protein and, in most cases, there is an optimal molecular weight PEG whereby an increase in the molecular weight PEG for that protein will not dramatically and/or at all change the dynamic binding potential. In an embodiment, a PEG is chosen with a molecular weight between about PEG 400 and about PEG 10000. In other embodiments, a mixture of different sized PEG is utilized. In a preferred embodiment, a PEG of molecular weight about PEG 4600 is utilized.

The concentration of the PEG in the solution may vary. Generally, any concentration PEG may be used. In an embodiment, concentration of the PEG in solution is between about 0.5% W/v PEG and about 6% w/v PEG. An ideal concentration of PEG for a particular protein can be determined by adding progressively greater concentrations of PEG during loading of the resin until an acceptable amount of precipitation is noted. In embodiments where precipitation is noted, the solution should be filtered.

Varying embodiments of the present invention utilize various ionic resins. In an embodiment, a cationic resin is used. In an alternate embodiment, an anionic resin is used.

In preferred embodiments, the exchanger(s) and/or resin(s) are located in column, as is common in the art.

The solutions of the present invention may have a wide variety of pH values. These differing pH values are often dependent upon the type of ionic resin. In general, for a cationic resin, the equilibration/load pH is typically less than about 8.0. Likewise, for anionic resins, the equilibration/load pH is greater than about 5.8. However, the pH used will be dependant upon the inherent properties of the protein, such as the pI, and may be higher or lower than these examples given. In an embodiment, the ion exchanger is a cation resin at a pH of about 5.0. In an alternate embodiment, the ion exchanger is an anion resin at a pH of about 8.0.

Further embodiments of the load solution of the present invention may be diluted to any volume, such dilution assisting to lower the salinity and/or conductivity of the solution.

Any protein may be used with the various embodiments of the invention. In an embodiment, proteins are chosen for biological research. In an alternate embodiment, proteins are chosen for purification. In an alternate embodiment, the protein comprises of any one of bovine γ-globulin, bovine serum albumin, and lysozyme. By illustrating the utility of the invention with commonly available proteins, it is readily obvious that other proteins may be used, as would be apparent to one of ordinary skill in the art.

Various embodiments of the invention exist as to how to load a protein onto the resin. In an embodiment, the protein is added to the solution and loaded onto the column in the feed stream. In other embodiments, the protein is added after the column is buffered and/or washed.

Other embodiments of the present invention comprise equilibrating the resin with a binding buffer before loading of the solution onto the resin.

Further processes of the present invention include a process for the separation of a protein of interest from a cell culture broth added to an ion exchange column comprising the steps of:
  a. increasing the dynamic binding capacity of an ion exchange resin by adding polyethylene glycol (PEG) to the cell culture broth;
  b. loading the resin with the cell culture broth whereby the protein of interest is at least partially captured; and,
  c. separating the protein of interest.

Other embodiments of the present invention comprise a recombinant protein source.

Compositions of the present invention comprise a solution comprising a cell culture broth that has high salinity, a PEG which is between about 1% w/v and 8% w/v, and a protein; and a resin, whereby said solution increases the dynamic binding capacity of the resin, thereby allowing the protein to be captured by the resin.

While the invention has been described in connection with specific embodiments thereof, it will be understood that it is capable of further modifications and the appended Claims are intended to cover any variations, uses, or adaptations of the invention following, in general, the principles of the invention and including such departures from the present disclosure as come within known or customary practice within the art to which the invention pertains and as may be applied to the essential features hereinbefore set forth whether now existing or after arising. Further, while embodiments of the invention have been described with specific dimensional characteristics and/or measurements, it will be understood that the embodiments are capable of different dimensional characteristics and/or measurements without departing from the principles of the invention and the appended Claims are intended to cover such differences. Furthermore, all patents and other publications mentioned herein are hereby incorporated by reference.

For a further understanding of various embodiments of the present invention, reference should be had to the following examples:

EXAMPLES

Example 1

Product Source for Experiments

Fractogel SO3 resin was obtained from EM Industries (Darmstadt, Germany) and SP Sepharose FF resin was obtained from Amersham Pharmacia Biotech (Piscataway, N.J., USA) and the column volumes were 10 ml (1.6×5 cm). Purified bovine γ-globulin was purchased from Calbiochem (San Diego, Calif., USA). PEG 400 and 10,000 were purchased from Aldrich Chemical (Milwaukee, Wis., USA). PEG 4600 was obtained from Union Carbide (Danbury, Conn., USA). Mammalian cell culture media Excell 301 was obtained from JRH Biosciences (Denver, Pa., USA). Buffer salts and additional culture media components were purchased from J. T. Baker (Phillipsburg, N.J. USA) and from Sigma (St. Louis, Mo. USA).

Experimental Procedure:

Experiments were conducted in a binding buffer of 50 mM sodium phosphate/citrate buffer, pH 5.0, or otherwise indicated, and step eluted with same buffer containing 0.5M sodium chloride. The load was prepared by dissolving purified bovine γ-globulin in Excell 301 media containing 1% Hysoy, 4 mM glutamine, 3 g/L glucose, 10 ml/L lipid 2 (Sigma) and 1.2 g/L sodium bicarbonate to mimic the harvest broth. A series of experiments were conducted with different loading conditions, including pH, dilution or PEG type and concentration. The run format used through the study was to pre-equilibrate the column first with 3 column volumes (CV) of 3-fold concentrated base binding buffer, and then equilibrate with 5 CV of binding buffer. Various amounts of purified bovine γ-globulin were loaded, washed with 5 CV binding buffer, and eluted in 5 CV binding buffer containing 0.5 M sodium chloride. Columns were stripped with an additional 3 CV 1M sodium chloride. All experiments were conducted at linear velocity of 150 cm/h at room temperature. Eluted bovine γ-globulin was immediately pH adjusted to 8.0 with 2M Tris base after pooling fractions. The bovine γ-globulin amount was quantitatively determined by an affinitive assay using analytical Poros Protein G column (4.6×100 mm, Applied Biosystems, Framingham Mass., USA).

1. pH Range Finding

Bovine γ-globulin was dissolved in Excell 301 media at a concentration of approximately 1 g/L, pH 7.4. The conductivity of this preparation was around 16 mS/cm, which is usually too high for a cation exchanger to bind γ-globulins. The binding buffer was tested at pH 6.5, 6.0, 5.5 and 5.0. The pH of the load was always the same as that of the equilibration buffer in the experiments. The load was filtered with 0.22μ filter to remove possible precipitation generated in the pH adjustment. With the loading pH range from 6.5 to 5.5, the majority of the bovine γ-globulin (>90%) was contained in the flow-through from both tested resins. pH 5.0, Fractogel SO3 showed significant decrease of bovine γ-globulin in the flow-through profile (from over 90% to 69%). SP Sepharose FF also showed a slight decrease of bovine γ-globulin in flow-through profile at pH 5.0. The results of this study are summarized in FIG. 1.

Most antibodies have a pI of around 8. When the pH is below the pI point, the protein is positively charged and in general can bind to cation exchanger resins under low conductivity conditions. As pH is lowered, typically the capacity of the resin to bind antibodies is increased. pH 5.0 is a reasonable starting point for observing the dynamic binding capacity change on cation exchanger resins for bovine γ-globulin. It contained approximately 30% of the total loading bovine γ-globulin recovered in elution profile from Fractogel SO3 column and 7% from SP Sepharose FF column. The poor overall recovery illustrates the need for better binding conditions, and thus provides adequate conditions to test the effect of conductivity and PEG addition on the resin dynamic binding capacity for future experiments.

2. Loading Conductivity Study

In order to find the actual dynamic binding capacity of testing resins to bovine γ-globulin, lowering the conductivity by diluting the feed-stream was tested in this experiment. Approximately 100 mg bovine γ-globulin at pH 5.0 was applied to the 10 ml column in each run. The conductivity of loading samples is listed below.

| Dilution Factor | No Dilution | 1:0.5 | 1:1 | 1:2 | 1:3 |
|---|---|---|---|---|---|
| Conductivity (mS/cm) | 15.74 | 11.08 | 8.74 | 5.59 | 4.48 |

The recovery of bovine γ-globulin with different diluted loading from both tested resins is demonstrated in FIG. 2. For Fractogel SO3, a loading dilution of 1:1 with water to bring the conductivity to around 8 to 9 mS/cm was sufficient to give maximum bovine γ-globulin recovery (~80%). For SP Sepharose FF, a loading dilution of 1:2 with water brought the conductivity down to around 5-6 mS/cm and maximized bovine γ-globulin recovery (73.1%). The similar outcome with further dilution was obtained from SP Sepharose FF.

At pH 5, most antibodies are positively charged and therefore can bind to the cation exchange columns. However, the conductivity in the harvested culture broth usually is too high for antibodies to bind to the resins as illustrated in the previous examples. The results demonstrate that decreasing the loading conductivity may make the binding of bovine γ-globulin to cation exchange resins more efficient under tested conditions. The maximum recovery for Fractogel SO3 was around 80% at conductivity below 9 mS/cm, for SP Sepharose FF was around 73% at conductivity below 6 mS/cm. Of note, in addition to the substantial volume increase some yield loss is still observed.

3. PEG 4600 Addition Study

We observed that polyethylene glycol (PEG) could increase the dynamic binding capacity of ion exchange resins under high conductivity conditions. In this experiment, PEG 4600 was added into the Excel 301 media containing 1 g/L bovine γ-globulin at pH 5.0. The PEG concentration in loading was 0.5, 1, 2, 4 and 6%. Precipitation was observed when the PEG 4600 concentration was over 2%. The load was filtered by 0.22μ filter and the bovine γ-globulin concentration in the load was confirmed before the feed applying to the column.

With increasing concentration of PEG 4600 in the load, the tested cation exchange resins showed significant increased binding capacity to bovine γ-globulin. By 6% w/v of PEG 4600 in the load, the Fractogel SO3 captured over 75% of bovine γ-globulin from load to elution as compared to less than 20% of bovine γ-globulin without PEG 4600. The SP Sepharose FF captured over 50% of bovine γ-globulin from load to elution with 6% w/v PEG 4600 and only ~10% without PEG 4600. With the PEG 4600 addition, the dynamic binding capacity of Fractogel SO3 to bovine γ-globulin was similar to that achieved with water dilution, 76.68% vs. 81.12%, without the increased volume associated with dilution. The binding capacity of SP Sepharose FF was below that achieved with water dilution, 53.16% vs. 73.06%. However, it showed a significant binding capacity increase compared to the same loading without PEG addition, from 7.46% to 53.16%. The results of this experiment were summarized in FIG. 3.

Addition of PEG 4600 in the load without dilution significantly increased binding capacity of cation exchange resins to bovine γ-globulin under the tested conditions. PEG seemingly masked the high conductivity influence on cation exchange resins with binding capacities similar to diluted loads easily achievable. Fractogel SO3 demonstrated enhanced capture as a function of PEG concentration as compared to SP Sepharose FF, likely due to its inherent higher affinity for bovine γ-globulin. Higher concentration of PEG 4600 caused protein precipitation for this experiment.

4. PEG Type Study

The addition of PEG 4600 in the feed stream revealed significant binding capacity increases for cation exchange chromatography of bovine γ-globulin. The function of the size of the PEG was investigated using 6% w/v PEG 400, and 6% w/v PEG 10000 as compared to 6% w/v 4600 to ascertain dependence of binding capacity increase on PEG size. 6% w/v different size of PEG was added to 1 g/L bovine γ-globulin in Excell 301 media, pH 5.0. Under the same tested conditions, 6% w/v PEG 400 in the load only slightly increased the cation exchange capacity for bovine γ-globulin. It showed 37.17% antibody recovery on Fractogel SO3 compared to approximately 20% on same resin without PEG 400 addition, and 7.89% on SP Sepharose FF comparing to 7.46%. PEG 10K showed the similar function as obtained from PEG 4600, with a slight lower level of increase. The data are summarized in FIG. 4.

Small PEG size, such as PEG 400, did not provide the significant binding capacity increase for the cation exchange resins for bovine γ-globulin whereas the large PEG size, such as PEG 10K, provided the additional binding capacity, same as observed from PEG 4600. This result may be related to the hydrating properties of PEG. Larger PEG molecules usually have stronger hydration capability. The lower binding capacity increment by PEG 10K in this experiment could be attributed to the filtration before loading.

Example 2

Anion Exchanger for Bovine Serum Albumin

Product Source:

Fractogel TMAE resin was obtained from EM Industries (Darmstadt, Germany) and Q Sepharose FF resin was obtained from Amersham Pharmacia Biotech (Piscataway, N.J., USA) and the column volumes were 10 ml (1.6×5 cm). Purified bovine serum albumin (BSA) and PEG 1350 and 3350 were purchased from Sigma (St. Louis, Mo., USA). PEG 400 and 10,000 were purchased from Aldrich Chemical (Milwaukee, Wis., USA). PEG 4600 was obtained from Union Carbide (Danbury, Conn., USA). Buffer salts were purchased from J. T. Baker (Phillipsburg, N.J. USA) and from Sigma (St. Louis, Mo. USA).

Experimental Procedure:

Experiments were conducted in a binding buffer of 50 mM Tris-HCl buffer, pH 8.0, or otherwise indicated, and step elution with same buffer at pH 7.5 containing 0.5M sodium chloride. The loading was prepared by dissolving purified BSA in binding buffer containing 150 mM sodium chloride to provide a high conductivity environment, for example recombinant expression harvest broth. A series of experiments were conducted with different loading conditions, such as various pH, dilution or PEG concentration and type, which are indicated in the results section. The run format used through the study was to pre-equilibrate the column first with 3 column volumes (CV) of 2-fold concentrated binding buffer, and then equilibrate with 5 CV of binding buffer. Approximately 200 mg BSA was loaded, washed with 5 CV binding buffer, and eluted in 5 CV elution buffer. Columns were stripped with additional 3 CV of 1M sodium chloride. All experiments were conducted at linear velocity of 150 cm/h at room temperature. The BSA amount was quantitatively determined by UV absorbency at 280 nm.

1. pH Range Finding

The BSA was dissolved in 50 mM Tris-HCl buffer with 150 mM sodium chloride at a concentration of approximately 3 g/L, pH depending on experimental requirement. The conductivity of this preparation was around 16 mS/cm, which is usually too high for anion exchanger to bind BSA. The binding buffer was tested at pH 7.2, 7.5 and 8.0. The pH of loading was made the correspondent change in the experiments. When the loading pH range from 7.2 to 7.5, the majority of the BSA (>80%) was contained in the flow-through from Fractogel TMAE and >70% for Q Sepharose FF. Only at pH 8.0, Fractogel TMAE showed a slight decrease of BSA in the flow-through profile to 74%. Q Sepharose FF also showed a decrease of BSA in flow-through profile to around 46% at pH 8.0. The results of this study were summarized in FIG. 5.

BSA has a theoretical pI of 5.82. When the working pH is higher than the pI point, the protein is negatively charged and in general can bind to anion exchange resins under mild conductivity conditions. As pH is increased, typically the capacity of the resin to bind BSA is increased. pH 8.0 was a reasonable start point for observing the dynamic binding capacity change on anion exchanger resins for BSA. It contained approximately 25% of the total loading BSA recovered in elution profile from Fractogel TMAE column and 53% from Q Sepharose FF column. The poor overall recovery illustrates the need for better binding conditions, and thus this result provided adequate conditions to test the effect of conductivity and PEG addition on the resin dynamic binding capacity for future experiments.

2. Loading Conductivity Study

In order to find the actual dynamic binding capacity of testing resins to BSA, lowering the conductivity by diluting the feed-stream was tested in this experiment. Approximately 200 mg BSA at pH 8.0 was applied to the 10 ml column in each run. The conductivity of loading samples is listed below.

| Loading buffer | 50 mM Tris-HCl w/150 mM NaCl | 50 mM Tris-HCl w/100 mM NaCl | 50 mM Tris-HCl w/66 mM NaCl |
|---|---|---|---|
| Conductivity (mS/cm) | 15.97 | 11.10 | 7.78 |

The recovery of BSA with different sodium chloride concentrations in load from both tested resins is demonstrated in FIG. 6. For Fractogel TMAE, a sodium chloride concentration of 66 mM to bring the conductivity around 7 to 8 mS/cm was sufficient to give maximum BSA recovery (~99.4%). For Q Sepharose FF, a loading with 100 mM sodium chloride brought the conductivity down to around 11 mS/cm and maximized BSA recovery (98.6%). Further dilution did not gain any recovery benefits.

At pH 8, BSA is negatively charged and therefore can bind to the anion exchange columns. However, the conductivity in the tested loading, which was selected to mimic that of harvested culture broth, is usually too high for BSA to bind to the resins as illustrated in the previous examples. The results demonstrated that decreasing the loading conductivity could make the binding of BSA to anion exchange resins more efficient under tested conditions, but at the sacrifice of significantly increasing the volume. The maximum BSA recovery for Fractogel TMAE was around 99% at conductivity below 7 mS/cm, also, for Q Sepharose FF was around 99% at conductivity below 11 mS/cm.

3. PEG 4600 Addition Study

We observed that polyethylene glycol (PEG) could increase the dynamic binding capacity of cation exchange resins under high conductivity conditions in Example 1. In this experiment, PEG 4600 was added into the Tris-HCl buffer with 150 mM NaCl and containing 3 g/L BSA at pH 8.0. The PEG concentrations in load were 0, 2, 4 and 6%. No precipitation was observed while adding the PEG 4600 to the desired concentration.

With increasing concentration of PEG 4600 in the load, the tested anion exchange resins showed significant increased binding capacity to BSA. By 6% w/v of PEG 4600 in the load, the Fractogel TMAE captured approximately 94% of BSA from load to elution as compared to approximately 25% of BSA without PEG 4600. The Q Sepharose FF captured the full BSA from load to elution with 4% w/v PEG 4600 and only 50% without PEG 4600. With the PEG 4600 addition, the dynamic binding capacity of Fractogel TMAE to BSA was slightly below to that achieved with water dilution, 94.19% vs. 99.37%. The binding capacity of Q Sepharose FF was similar to that achieved with water dilution, 99.1% vs. 98.6%. The results of this experiment were summarized in FIG. 7.

Addition of PEG 4600 in the load without dilution significantly increased binding capacity of anion exchange resins to BSA under the tested conditions. PEG seemingly masked the high conductivity influence on anion exchange resins with binding capacities similar to diluted loads easily achievable. Reasonable concentration of PEG 4600, 6% w/v for Fractogel TMAE and 4% w/v for Q Sepharose FF, the load was sufficient to achieve the maximum BSA binding in this example.

4. PEG Type Study

In addition of PEG 4600, the function of the size of the PEG was investigated using 6% w/v PEG 400, and 4% w/v PEG 1450, 3350 and 10000 as compared to 4% w/v 4600 to ascertain dependence of binding capacity increase on PEG size. PEG was added to 3 g/L BSA in 50 mM Tris-HCl buffer containing 150 mM NaCl, pH 8.0. Under the same tested conditions, 6% w/v PEG 400 in the load increased the anion exchange capacity for BSA significantly. It showed 54.69% BSA recovery on Fractogel TMAE compared to 25.49% on same resin without PEG 400 addition, and 95.95% on Q Sepharose FF comparing to 51.35% with no PEG addition. With the increment of PEG sizes, a proportional dynamic binding capacity increasing on Fractogel TMAE to BSA was observed. PEG 10K showed the similar function as obtained from PEG 4600, with a very minor level of increment (79.31% vs. 80.95%). The data obtained from Q Sepharose FF column were inconclusive because of the high start point of binding. The data of this experiment were summarized in FIG. 8.

PEG generally could provide the binding capacity increment for the anion exchange resins to BSA. The increment of binding capacity is proportionally to the size of the PEG up to approximately 4600 daltons. This result may be related to the hydrating properties of PEG. Larger PEG molecules usually have stronger hydration capability. However, PEG 10K only made a slightly difference comparing to PEG 4600 (80.95% vs. 79.31%) on Fractogel TMAE to BSA. There was no precipitation observed during the preparation of BSA/PEG loading. It seemed that smaller protein (comparing to bovine γ-globulin) could take higher PEG concentration. However, it was unnecessary for the column binding capacity in this particular case.

Example 3

Cation Exchanger for Lysozyme

Product Source:

Fractogel SO3 resin was obtained from EM Industries (Darmstadt, Germany) and SP Sepharose FF resin was obtained from Amersham Pharmacia Biotech (Piscataway, N.J., USA) and the column volumes were 10 ml (1.6×5 cm). Purified lysozyme was purchased from Roche (Indianapolis, Ind., USA). PEG 400 and 10,000 were purchased from Aldrich Chemical (Milwaukee, Wis., USA). PEG 4600 was obtained from Union Carbide (Danbury, Conn., USA). Buffer salts were purchased from J. T. Baker (Phillipsburg, N.J. USA) and from Sigma (St. Louis, Mo. USA).

Experimental Procedure:

Experiments were conducted in a binding buffer of 50 mM sodium phosphate/citrate buffer, pH 7.0, or otherwise indicated, and step elution with same buffer containing 0.5M sodium chloride. The loading was prepared by dissolving purified lysozyme in base binding buffer containing 150-250 mM sodium chloride. A series of experiments were conducted with different loading conditions, such as various pH, salt concentration or PEG concentration and type, which are indicated in the results section. The run format used through the study was to pre-equilibrate the column first with 3 column volumes (CV) 3-fold concentrated binding buffer, and then equilibrate with 5 CV of binding buffer. Approximately 200 mg purified lysozyme was loaded, washed with 5 CV binding buffer, and eluted in 5 CV elution buffer. Columns were stripped with an additional 3 CV of 1M sodium chloride. All experiments were conducted at linear velocity of 150 cm/h at room temperature. The lysozyme amount was quantitatively determined by UV absorbance at 280 nm.

Results and Discussion 1. pH Range Finding

The lysozyme was dissolved at a concentration of 3 g/L in binding buffer containing 150 mM sodium chloride to produce a high salt condition. The binding buffer was tested at pH 5.5, 6.0, 6.5 and 7.0. The pH of loading was made the correspondent change in the experiments. At all tested pH ranges, lysozyme showed excellent binding to both columns. The loaded lysozyme was almost fully recovered (over 99%) at tested pHs, except for SP Sepharose FF at pH 7.0, it was 94%. In order to find out a reasonable start point condition with appropriate distribution of model protein in flow through and elution profiles, pH 7.0 was used to test higher salt concentrations.

2. Loading Conductivity Study

In order to find a reasonable start point of dynamic binding capacity on testing resins to lysozyme at pH 7.0, increasing the salt concentration in feed-stream was tested. Approximately 200 mg lysozyme in binding buffer at pH 7.0 was applied to the 10 ml column in each run. The conductivity of loading samples is listed below.

| Salt concentration | 150 mM NaCl | 200 mM NaCl | 250 mM NaCl |
|---|---|---|---|
| Conductivity (mS/cm) | 19.56 | 23.18 | 27.31 |

The flow through lysozyme with different loading from both tested resins is demonstrated in FIG. 9. For Fractogel SO3, a loading with 250 mM NaCl to bring the conductivity around 27 mS/cm was sufficient to give 7.4% lysozyme in the flow through. With the same salt concentration in the load, SP Sepharose FF showed 74.5% lysozyme in the flow through profile. This result provided adequate conditions to test the effect of conductivity and PEG addition on the resin dynamic binding capacity for future experiments.

3. PEG 4600 Addition Study

We observed that PEG could increase the dynamic binding capacity of ion exchange resins under high conductivity conditions (Example 1 and 2). This experiment was targeted to the small size of model protein, lysozyme (MW: ~14.5 kD), to observe the function of PEG 4600. PEG 4600 was added into the load with 250 mM NaCl containing 3 g/L lysozyme at pH 7.0. The PEG concentration in loading was 0, 2, 4 and 6%, respectively.

With increasing concentration of PEG 4600 in the load, the tested cation exchange resins showed very slightly increased binding capacity of lysozyme. Comparing 6% w/v of PEG 4600 and no PEG in the load, the BSA recovery showed only less than 2% increase (92.75% vs. 90.84%) by the Fractogel SO3 column. The similar observation was obtained from SP Sepharose FF column (26.24% vs. 23.02%). The results of this experiment are summarized in FIG. 10.

Addition of PEG 4600 in the load without dilution did not appreciably increase binding capacity of cation exchange resins to lysozyme. The function of PEG 4600 masked the high conductivity influence on cation exchange resins. It could be attributed by small surface of the model protein that PEG could not provide significant dehydration on it.

4. PEG Type Study

The function of the size of the PEG was investigated using 6% w/v PEG 400, and 6% w/v PEG 10000 as compared to 6% w/v 4600 to ascertain dependence of binding capacity change on PEG size. 6% w/v different size of PEG was added to 3 g/L lysozyme in 50 mM citrate/phosphate buffer with 250 mM NaCl, pH 7.0. Comparing to the test without PEG, instead increased the cation exchange capacity for lysozyme, both tested resins decreased the binding capacity to lysozyme with 6% w/v PEG 400 in the load under the same tested conditions. It showed only 76.32% lysozyme recovery on Fractogel SO3 compared to 90.84% on same resin without PEG 400 addition, and 16.56% on SP Sepharose FF comparing to 23.02%. PEG 10K showed the similar function as obtained from PEG 4600, with a slight lower level of increment. The data were summarized in FIG. 11.

Small PEG size, such as PEG 400, did not provide the binding capacity increment for the cation exchange resins for lysozyme whereas the large PEG size, such as PEG 10K, provided the slightly better binding capacity observed for PEG 4600. This result may be related to the hydrating properties of PEG and surface size of tested model proteins.

What is claimed is:

1. A process for protein purification by ion exchange chromatography from a protein solution having a salt concentration sufficient to significantly reduce the binding of the protein to the ion exchange resin, the process, comprising the steps of:
   a. adding from about 0.5% w/v to about 6% w/v polyethylene glycol (PEG) to a protein solution having a salt concentration sufficient to significantly reduce the binding of the protein to an ion exchange resin to form a protein-PEG solution; and,
   b. binding the protein to the ion exchange resin by contacting the ion exchange resin with the protein-PEG solution.

2. The process of claim 1, wherein the protein solution is a cell culture broth.

3. The process of claim 1, wherein the PEG is chosen with a molecular weight between about PEG 400 and about PEG 10000, and mixtures thereof.

4. The process of claim 1, wherein the PEG is PEG 4600.

5. The process of claim 1, wherein the ion exchange resin is a cationic exchange resin.

6. The process of claim 5, wherein the conductivity of the protein-PEG solution is greater than about 9 mS/cm.

7. The process of claim 1, wherein the ion exchange resin is an anionic exchange resin.

8. The process of claim 7, wherein the conductivity of the protein-PEG solution is greater than about 11 mS/cm.

9. The process of claim 1, wherein the binding of the protein to the ion exchange resin occurs about a column.

10. The process of claim 1, wherein the step of contacting is at a pH in a range of about 4.0 to about 10.0.

11. The process of claim 1, wherein the protein solution is diluted.

12. The process of claim 5, wherein the ion exchange resin is a cation exchanger at a pH of about 5.0.

13. The process of claim 1, wherein the protein is selected from the group consisting of bovine γ-globulin, bovine serum albumin, and lysozyme.

14. The process of claim 1, further comprising determining an ideal concentration of PEG for a particular protein by adding progressively greater concentrations of PEG to facilitate binding during loading of the resin until an acceptable amount of precipitation is observed.

15. The process of claim 1, further comprising filtering the protein-PEG solution.

16. The process of claim 1, wherein the step of binding the protein to the ion exchange resin is preceded by a step of equilibrating the ion exchange resin with a binding buffer.

17. A process for the separation of a protein of interest by ion exchange chromatography from a cell culture broth having a salt concentration sufficient to significantly reduce the binding of the protein to the ion exchange resin, the process comprising the steps of:
   a. adding polyethylene glycol (PEG) to the cell culture broth to form a PEG-cell culture broth;
   b. binding the protein of interest to the ion exchange resin by contacting the ion exchange resin with the PEG-cell culture broth; and,
   c. separating the protein of interest from the PEG-cell culture broth.

18. The process of claim 17, wherein the protein of interest is a recombinant protein.

19. The process of claim 17, wherein the ion exchange resin is either a cation exchange resin or an anion exchange resin.

20. The process of claim 17, further comprising the step of determining an ideal concentration of PEG for a particular protein by adding progressively greater concentrations of PEG to facilitate binding during loading of the resin until an acceptable amount of precipitation is noted.

21. A mixture comprising an ion exchange resin and a solution comprising a cell culture broth, polyethylene glycol (PEG) in an amount which is between about 1% w/v and 8% w/v of the cell culture broth, and a protein;
   wherein
      the protein is bound to the ion exchange resin, and
      the cell culture broth has a salt concentration sufficient to significantly reduce the binding of the protein to the ion exchange resin in the absence of the PEG.

22. The mixture of claim 21, wherein the ion exchange resin is a cationic ion exchange resin and the conductivity of the solution is greater than about 9.

23. The mixture of claim 21, wherein the ion exchange resin is an anionic ion exchange resin and the conductivity of the solution is greater than about 11.

* * * * *